United States Patent [19]

Ohno et al.

[11] Patent Number: 5,618,922

[45] Date of Patent: Apr. 8, 1997

[54] NM03 ANTIBODY MATERIALS AND METHODS

[75] Inventors: Tsuneya Ohno; Masaki Terada, both of Boston, Mass.; Yukio Yoneda, Ohtsu, Japan

[73] Assignee: Nissin Shokuhin Kabushiki Kaisha, Osaka, Japan

[21] Appl. No.: 279,906

[22] Filed: Jul. 25, 1994

[51] Int. Cl.⁶ ............ C07K 16/08; C07K 16/10; C12P 21/08

[52] U.S. Cl. ............ 530/388.35; 530/387.9; 435/331; 435/339.1; 424/148.1

[58] Field of Search ............ 530/388.35, 387.9; 435/240.27; 424/148.1

[56] References Cited

U.S. PATENT DOCUMENTS 5,019,387  5/1991  Haynes et al.

FOREIGN PATENT DOCUMENTS

| | | |
|---|---|---|
| WO88/09181 | 12/1988 | WIPO |
| WO90/12868 | 11/1990 | WIPO |
| WO90/15078 | 12/1990 | WIPO |
| WO91/09625 | 7/1991 | WIPO |
| WO91/11198 | 8/1991 | WIPO |
| WO91/19797 | 12/1991 | WIPO |
| WO93/04090 | 3/1993 | WIPO |

OTHER PUBLICATIONS

Akerblom et al., "Neutralizing cross-reactive and non-neutralizing monoclonal antibodies to HIV-1 gp120", *AIDS*, 4:953–960 (1990).

Albovini et al., Eds., "Detection of HIV in Clinical Specimens", pp. 15–29 in *Techniques in HIV Research*, Stockton Press, New York, New York (1990).

Durda et al., "HIV-1 Neutralizing Monoclonal Antibodies Induced by a Synthetic Peptide", *AIDS Research and Human Retroviruses*, 6:1115–1123 (1990).

Emini et al., "Prevention of HIV-1 Infection in Chimpanzees by gp120 V3 Domain-Specific Monoclonal Antibody", *Nature*, 335:728–730 (1992).

Godding, "Antibody Production by Hybridomas", *J. Immunol. Meth.*, 39:285–308 (1980).

Goudsmit et al., "Human Immunodeficiency Virus Type 1 Neutralization Epitome With Conserved Architecture Elicits Early Type–Specific Antibodies in Experimentally Infected Chimpanzees", *Proc. Natl. Acad. Sci. USA*, 85:4478–4482 (1988).

Haigwood et al., "Evidence for Neutralizing Antibodies Directed Against Conformational Epitopes of HIV-1 gp120", *Vaccines*, 90:313–320 (1990).

Ho et al., "Conformational Epitope on gp120 Important in CD4 Binding and Human Immunodeficiency Virus Type 1 Neutralization Identified by a Human Monoclonal Antibody", *J. Virol.*, 65(1):489–493 (1991).

Ho et al., "Second Conserved Domain of gp120 Is Important for HIV Infectivity and Antibody Neutralization", *Science*, 239:1021–1023 (1988).

Holley et al., "Prediction of Optimal Peptide Mixtures to Induce Broadly Neutralizing Antibodies to Human Immunodeficiency Virus Type 1", *Proc. Natl. Acad. Sci. USA*, 85:6800–6804 (1991).

Jackson et al., "Passive Immunoneutralisation of Human Immunodeficiency Virus in Patients with Advanced AIDS", *Lancet*, 2:647–652 (1988).

Javaherian et al., "Broadly Neutralizing Antibodies Elicited by the Hypervariable Neutralizing Determinant of HIV–1", *Science*, 250: 1590–1593 (1990).

Javaherian et al., "Principal Neutralizing Domain of the Human Immunodeficiency Virus Type I Envelope Protein", *Proc. Natl. Acad. Sci. USA*, 86:6768–6772 (1989).

Karpas et al., "Effects of Passive Immunization in Patients with the Acquired Immunodeficiency Syndrome–Related Complex and Acquired Immunodeficiency Syndrome", *Proc. Natl. Acad. Sci. USA*, 85:9234–9237 (1988).

LaRosa et al., "Conserved Sequence and Structural Elements in the HIV–1 Principal Neutralizing Determinant", *Science*, 249:932–935 (1990).

Lasky et al., "Neutralization of the AIDS Retrovirus by Antibodies to a Recombinant Envelope Glycoprotein", *Science*, 233: 209–212 (1986).

Liou et al., "A Chimeric Mouse–Human Antibody that Retains Specificity for HIV gp120 and Mediates the Lysis of HIV–Infected Cells", *J. Immunol.*, 143(12):3967–3975 (1989).

Matsushita et al., "Characterization of a Human Immunodeficiency Virus Neutralizing Monoclonal Antibody and Mapping of the Neutralizing Epitope", *J. Virol.*, 62:2107–2114 (1988).

McCune, "HIV–1: The Infective Process in Vivo", *Cell*, 645:351–363 (1991).

Ohno et al., "A broadly neutralizing monoclonal antibody that recognizes the $V_3$ region of human immunodeficiency virus type 1 glycoprotein gp120", *Proc. Natl. Acad. Sci. USA*, 88:10726–10729 (1991).

Oi and Herzenberg, "Immunoglobulin–Producing Hybrid Cell Lines", *Selected Methods Cell Immunology*: 351–372 (1979).

Palker et al., "Type–specific Neutralization of the Human Immunodeficiency Virus with Antibodies to Env–encoded Synthetic Peptides", *Proc. Natl. Acad. Sci. USA*, 85:1932–1936 (1988).

Putney et al., "HTLV–III/LAV–Neutralizing Antibodies to an *E. Coli*–Produced Fragment of the Virus Envelope", *Science*, 234:1392–1395 (1986).

Rusche et al., "Antibodies That Inhibit Fusion of Human Immunodeficiency Virus–Infected Cells Bind a 24–Amino Acid Sequence of the Viral Envelope", *Proc. Natl. Acad. Sci. USA*, 85:3198–3202 (1988).

(List continued on next page.)

*Primary Examiner*—Toni R. Scheiner
*Attorney, Agent, or Firm*—Marshall, O'Toole, Gerstein, Murray & Borun

[57] ABSTRACT

The present invention provides a monoclonal antibody, designated NM03, which specifically binds HIV-1 gp 120.

5 Claims, No Drawings

OTHER PUBLICATIONS

Scott et al., "Human Monoclonal Antibody That Recognizes the V3 Region of Human Immunodeficiency Virus gp120 and Neutralizes the Human T–Lymphoctropic", *Proc. Natl. Acad. Sci. USA*, 87:8597–8601 (1990).

Weiss et al., "Variable and Conserved Neutralization Antigens of Human Immunodeficiency Virus", *Nature*, 324:572–575 (1986).

Cohen Science vol. 264. 20 May 1994 p. 1072.

Fahey et al. Clin Exp. Immunol. 1992 88 1–5.

NM03 ANTIBODY MATERIALS AND METHODS

FIELD OF THE INVENTION

The present invention relates, in general, to materials and methods useful in the prevention and treatment of Human Immunodeficiency Virus (HIV-1) infection. More particularly, the invention relates to monoclonal antibodies useful in passive immunization of HIV-1 susceptible or infected animals, especially humans.

BACKGROUND

The infective process of HIV-1 in vivo has been the subject of a review article by McCune, *Cell*, 64: 351–363 (1991). Briefly, HIV-1 infects a variety of cell lineages, such as T-cells, monocytes/macrophages and neuronal cells, which express the CD4 receptor. Because the vast majority of $CD4^+$ cells in the body are "resting" or quiescent and divide only in response to specific signals, infection with HIV-1 results in $CD4^+$ cells harboring transcriptionally inactive virus. Stimulation of the immune system of infected animals, including active immunization, may result in polyclonal activation and the signaling of resting $CD4^+$ cells to go into the S phase of the cell cycle. The replicating cells then actively produce viral particles, provoking spread of the infection. Considering this negative effect of stimulating the immune system of an HIV-1-infected animal, it is possible that the most effective method of preventing or treating HIV-1 infection is passive immunization, that is, administering anti-HIV-1 antibodies to a susceptible or infected animal.

Jackson et al., *Lancet*, 2: 647–652 (1988) reports that a single administration of anti-HIV-1 antibodies in the form of plasma to human patients afflicted with advanced acquired immunodeficiency syndrome (AIDS, the syndrome of progressive immune system deterioration associated with HIV-1 infection) temporarily resulted in: fewer symptoms, a transient increase in T lymphocytes, a reduction in the frequency of opportunistic infections and a decline in the rate at which HIV-1 could be cultured from plasma or lymphocytes of the patients. See also, Karpas et al., *Proc. Natl. Acad. Sci. USA*, 85: 9234–9237 (1988). Moreover, Emini et al., *Nature*, 355: 728–730 (1992) reports that the administration of an antibody specifically reactive with HIV-1 to a chimpanzee before the animal was exposed to HIV-1 resulted in the chimpanzee remaining free of signs of viral infection. These studies indicate that antibodies capable of neutralizing HIV-1 can be useful in the prevention/treatment of HIV-1 infection.

The HIV-1 major external envelope glycoprotein, gp120, binds to the cellular CD4 receptor and facilitates the internalization of the virus. Several epitopes of the glycoprotein have been associated with the development of neutralizing antibodies. Ho et al., *Science*, 239: 1021–1023 (1988) reports that amino acids 254–274 of gp120 elicit polyclonal antisera capable of group-specific neutralization of three different isolates of HIV-1. Conformation-dependent epitopes, epitopes not consisting of primary sequences of amino acids, on gp120 have also been implicated in eliciting antibodies that neutralize diverse strains of the virus by Haigwood et al., *Vaccines* 90: 313–320 (1990) and Ho et al., *J. Virol.*, 65(1): 489–493 (1991). The so-called "principal neutralizing determinant" (PND) of HIV-1 gp120 has been localized to the "$V_3$ loop" of gp120. See Putney et al., *Science*, 234: 1392–1395 (1986); Rusche et al., *Proc. Natl. Acad. Sci. USA*, 85: 3198–3202 (1988); Goudsmit et al., *Proc. Natl. Acad. Sci. USA*, 85: 4478–4482 (1988); Palker et al., *Proc. Natl. Acad. Sci. USA*, 85: 1932–1936 (1988); and Holley et al., *Proc. Natl. Acad. Sci. USA*, 85: 6800–6804 (1991). The $V_3$ loop consists of a hypervariable domain which is established by disulfide bonding between cysteine residues flanking the domain. The $V_3$ loop of HIV-$1_{MN}$, for example, is formed by a disulfide bond between the cysteine residues at positions 302 and 336 of gp120.

Recombinant and synthetic protein fragments including the series of amino acid residues of the $V_3$ loop from various HIV isolates have been reported to elicit isolate- or type-specific neutralizing antibodies in rodents by Lasky et al., *Science*, 233: 209–212 (1986); Palker et al., supra; Matsushita et al., *J. Virol.*, 62: 2107–2114 (1988); and Javaherian et al., *Proc. Natl. Acad. Sci. USA*, 86: 6768–6772 (1989). More recent studies [Putney et al., supra and LaRosa et al., *Science*, 249: 932–935 (1990)] have demonstrated that the β-turn structure of the $V_3$ loop is the site recognized by the isolate-specific antibodies. Scott et al., *Proc. Natl. Acad. Sci. USA*, 87: 8597–8601 (1990) report that the PND can also induce a type-specific antibody in humans. The hypervariability of the PND may account for the type-specific neutralizing activity generated by the epitope.

Several studies have suggested that antibodies prepared against recombinant gp120, purified gp120 or synthetic peptides from $V_3$ domain can neutralize diverse HIV-1 isolates. Javaherian et al., *Science*, 250: 1590–1593 (1990) and Weiss et al., *Nature*, 324: 572–575 (1986) each describe neutralization of both MN and $III_B$ isolates by polyclonal sera from rabbits respectively immunized with a peptide corresponding to the PND of MN isolates and with a recombinant gp120 derived from a $III_B$ isolate. See also, Haynes et al., U.S. Pat. No. 5,019,387.

Akerblom et al., *AIDS*, 4: 953–960 (1990) describes monoclonal antibody preparations that neutralize $III_B$ and eleven primary HIV-1 isolates. See also, Patent Cooperation Treaty (PCT) Publication No. WO 91/11198 of Wahren et al., published on Aug. 8, 1991. The strain homology of the Akerblom primary isolates is not determined, however, and the eleven isolates may also be $III_B$. Durda et al, *AIDS Res. Hum. Retrov.*, 6: 1115–1123 (1990) report a monoclonal antibody that blocks syncytia formation by both MN- and $III_B$-infected cells, but does not neutralize MN infectivity as determined by a "LAV capture immunoassay," an assay which is purported to give results that would correlate with reverse transcriptase activity. Patent Cooperation Treaty Patent Application No. WO 90/15078 of Scott et al., published on Dec. 13, 1990, describes monoclonal antibodies which inhibit syncytium formation by cells infected with vaccinia virus expressing the PND of MN or "MN-like" isolates. None of the assertedly "broadly neutralizing" antibodies are demonstrated, by means of standard reverse transcriptase, p24 or MT-2 assays, to neutralize multiple strains of live HIV-1. See also, PCT Publication Nos. WO 88/09181, WO 90/12868, WO 91/09625 of Tanox Biosystems, Inc., published on Dec. 1, 1988, Nov. 1, 1990 and Jul. 11, 1991, respectively; PCT Publication No. WO 91/19797 of New York University, published on Dec. 26, 1991; and Liou et al., *J. Immunol.*, 143(12): 3967–3975 (1989). A broadly neutralizing antibody specific for the $V_3$ region of HIV-1 gp120, monoclonal antibody NM01, is described in Ohno et al., *Proc. Natl. Acad. Sci. USA*, 88: 10726–10729 (1991) and in PCT International Publication No. WO 93/04090 published on Mar. 4, 1993.

The foregoing publications indicate that monoclonal antibodies reactive with the HIV-1 PND developed to date exhibit different levels of group reactivity, but may not have broad neutralizing activity. The different patterns of type- and group-specific reactivity indicated by these studies may be related to both the amino acid sequence and the conformation of the loop region of gp120.

There thus continues to exist a need in the art for new monoclonal antibody substances (including, e.g., murine-derived antibodies, humanized antibodies, and immunologically active antibody fragments) which are specifically immunoreactive with HIV-1. Ideally, such antibodies would be characterized by the ability to effect neutralization of multiple HIV-1 strains as determined by standard p24 assays involving suitable cultured host cells (e.g., H9 cells).

BRIEF SUMMARY

The present invention provides monoclonal antibodies which are specifically reactive with that portion of HIV-1 gp120 or gp160 protein comprising the amino acid sequence set out in SEQ ID NO: 1, alanine-phenylalanine-tyrosine-threonine-threonine-lysine-asparagine (A-F-Y-T-T-K-N), and are characterized by their capacity to neutralize the infection of H9 cells in culture by live HIV-1 strain MN as determined by p24 assays.

Monoclonal antibodies of the present invention may be used in diagnostic methods and/or kits to determine the presence of HIV-1 in a fluid (e.g., blood). Monoclonal antibodies according to the present invention, preferably IgM antibodies, are also particularly suitable for use in anti-HIV-1 treatment of animals, especially humans, susceptible to or infected with HIV-1. Immunologically effective amounts of the monoclonal antibodies are administered to a patient infected with HIV-1 or at risk of infection with the virus to develop passive immunity to HIV-1 infection.

"Humanized" antibodies (including chimeric and CDR-grafted antibodies), antibody fragments, and especially bi-specific antibodies based on the claimed monoclonal antibodies are within the contemplation of the present invention, as are recombinant antibody-related products produced in procaryotic or eucaryotic cells. For example, antibody fragments, such as Fab and F(ab')$_2$ fragments, can be produced in culture by host cells such as *E. coli*, yeast, insect and mammalian cells upon determination of structural (sequence) information for the variable regions of the antibodies of the invention. Sequence information for the variable regions also enables preparation of CDR-grafted antibodies. Moreover, chimeric antibodies (e.g., mouse/human antibodies) may be prepared using transformed mouse myeloma cells or hybridoma cells and bi-specific antibodies may be produced by hybrid hybridoma cells. Specifically contemplated are antibodies which consist essentially of a human antibody variable region comprising a sequence of amino acids of at least one complementarity determining region of an antibody characterized by the ability to specifically bind to a sequence of amino acids of HIV-1 gp120 or gp160 consisting essentially of the sequence set out in SEQ ID NO: 1 and the ability to neutralize, in vitro, the infection of H9 cells by live HIV-1 strain MN in p24 assays. DNA sequences encoding such antibodies, host cells producing such antibodies and recombinant methods for producing such antibodies are contemplated.

Also within the contemplation of the present invention is the use, in anti-HIV-1 treatment, of a combination of the products of the present invention and other immunological agents and/or chemical therapeutic agents. Potential agents for combined administration include complement, antibodies which bind to various neutralizing and non-neutralizing domains of HIV-1 proteins, and chemical agents such as AZT. Preferred non-peptidyl agents are described in co-owned, concurrently filed U.S. patent application Ser. No. 08/280,090 identified by attorney docket No. 31995.

As set forth in the following detailed description, monoclonal antibodies of the present invention were generated by immunization of an appropriate host with live HIV-1, thus presenting gp120 in its native conformation.

Specifically illustrating the present invention is the murine monoclonal antibody (designated NM03) produced by the hybridoma cell line which was received for deposit with the American Type Culture Collection, 12301 Parklawn Drive, Rockville, Md. 20852, on Apr. 13, 1994 and was assigned ATCC Accession No. HB 11614.

DETAILED DESCRIPTION

The following examples illustrate practice of the invention in the production of a hybridoma cell line HB 11614, the isolation therefrom of monoclonal antibodies immuno-reactive with HIV-1 gp120 (or its precursor gp160) proteins as well as peptides comprising the amino acid sequence A-F-Y-T-T-K-N set out in SEQ ID NO: 1, the characterization of such monoclonal antibodies.

More particularly, Example 1 is directed to the production of hybridoma cell line HB 11614 and the isolation of monoclonal antibody NM03 therefrom. Example 2 relates to the mapping of the viral epitope recognized by antibody NM03. Example 3 relates to the screening of antibody NM03 for the capacity to neutralize infection of H9 cells by various live HIV-1 strains as demonstrated by p24 assays.

EXAMPLE 1

Hybridoma cell line HB 11614 was produced using standard immunological techniques such as described in Oi and Herzenberg, *Selected Methods Cell Immunology*: 351–372 (1979) and Godding, *J. Immunol. Meth.*, 39: 285–308 (1980) and set out specifically below.

A. Purification of Live HIV-1$_{MN}$

Three hundred ml of HIV-1$_{MN}$-infected H9 cell culture was collected and centrifuged at 1500 rpm for 5 minutes at 4° C. to pellet the cells. The virus-containing supernatant was removed and saved, while the precipitate was recentrifuged at 2100 rpm for 20 minutes. The second supernatant was collected and pooled with the first, and the supernatant was ultracentrifuged in a SW 27 rotor at 25,000 rpm for 90 minutes at 4° C. to pellet the viral particles. The resulting supernatant was discarded. The viral pellet was resuspended in approximately 10 ml TNE buffer (100 mM NaCl, 10 mM Tris-Hcl, pH 7.7, 1 mM EDTA). An ultracentrifuge tube was prepared containing a bottom layer of 10 ml 50% sucrose TNE, a middle layer of 10 ml 25% sucrose TNE and a top layer of 10 ml virus sample, and was ultracentrifuged at 25,000 rpm at 4° C. for 90 minutes. The virus precipitated as a white band between the layers of sucrose TNE and was collected with a pasteur pipet. Twenty ml TNE/15 mM EDTA (100 mM NaCl, 10 mM Tris-HCl, pH 7.7, 15 mM EDTA) was added to the virus and the viral sample was spun again at 25,000 rpm at 4° C. for 90 minutes. The resulting pellet comprised purified live HIV-1$_{MN}$.

B. Immunization and Hybridoma Preparation

One hundred µg live HIV-1$_{MN}$ was used to immunize each of three two-month old Balb/c mice by intraperitoneal injection. The mice were each boosted 3 weeks later with 30 µg virus and again after another 3 weeks with 100 µg of the viral preparation. The mice were sacrificed 3 days after the second boost and hybridoma cell lines were prepared by fusing splenocytes with P3-X63-Ag8-U1 cells (ATCC CRL 1597). Hybridoma cells lines were also prepared from the spleens of mice immunized with chronically infected H9 cells (10 mice), acutely infected H9 cells (9 mice) and cell membranes from chronically infected H9 cells (3 mice). Chronically infected H9 cells are cells 2 to 3 weeks after infection having reverse transcriptase assay (RT) counts of 100,000 cpm to 150,000 cpm, while acutely infected H9 cells are cells 10 to 12 days after infection having RT counts of 200,000 cpm to 250,000 cpm.

The hybridoma cell lines were prepared by the following method. A mixture of spleen cells from immunized mice was spun at 800 g for 5 minutes. The supernatant was aspirated from the cell pellet and 1 ml warm (37° C.) 50% PEG-1500 per 10$^8$ cells was added to the pellet over a period of 1 minute (add 0.25 ml, stir gently with the pipet tip for 15 seconds and repeat). The mixture was stirred for an additional minute with the same pipet tip without breaking up cell clumps. One ml of "incomplete media" [RPMI 1640 (JRH Biosciences) supplemented with 25 mM HEPES (Sigma Co.), 100 U/ml penicillan and 100 mg/ml streptomycin] was then added over a period of 1 minute in the same manner (0.25 ml every 15 seconds) and another 1 ml was added over another minute. Next, 7 ml incomplete media was stirred in over a period of 2–3 minutes (1 ml every 20 seconds) resulting in a suspension of fine cell clumps. The final suspension was centrifuged at 500 g on a clinical centrifuge for 5 minutes and the supernatant was removed. The precipitate was resuspended by swirling (not vortexing or pipetting solution up and down) in "complete media" ["incomplete media" as above supplemented with 15% fetal calf serum (FBS)] to a concentration of 2×10$^6$ cells per ml media. Next, 0.1 ml of this suspension (2×10$^5$ total cells) was plated per well of 96-well plates. The plates were incubated at 37° C., 7% CO$_2$. The day of fusion was considered Day 0.

C. HAT Selection and Initial Screening of Hybridomas

Twenty-four hours after fusion (Day 1), 0.1 ml HAT media (10$^{-4}$M hypoxanthine, 5×10$^{-7}$M aminopterin and 1.6×10$^{-5}$M thymidine) was added to each well. On Days 2, 3, 5, 8, 11, 14, 17 and 21, 0.1 ml of media was removed from each well and replaced with fresh 0.1 ml HAT media. On Days 2 through 5, the wells appeared to contain only dead cells. Hybridomas began to appear between Days 5 and 10. The hybridomas were easily visible as colonies of very refractible cells surrounded by cellular debris.

D. Hybridoma Screening

Several assays were utilized for screening the hybridoma supernatants. Hybridomas secreting antibodies reactive with HIV-1 were initially identified by screening membranes prepared from non-infected and MN-infected H9 cells by ELISA with hybridoma culture supernatants. This initial screen was followed by immunofluorescence screening to supplement the ELISA data with antibody binding data to live infected cells.

Cell membranes for the ELISA were prepared from infected or noninfected H9 cells. The cells were suspended in a 250 mM sucrose/10 mM Tris-HCl buffer at pH 7.4 containing 1 mM EDTA. The suspension was homogenized in a Dounce homogenizer placed in an ice bath until no viable cells were seen by Trypan Blue exclusion. The mixture was centrifuged for 2 minutes at 50 g. The resulting pellet was rehomogenized and recentrifuged. The two supernatants were combined and centrifuged at 20,000 g for 20 minutes. The pellet was again homogenized in the same buffer and centrifuged for 20 minutes and the pellet resuspended in 7 ml of the original 250 mM sucrose-EDTA buffer. This solution was then layered over a 2M sucrose/10 mM Tris-HCl buffer containing 1 mM EDTA and centrifuged for 1 hour at 80,000 g. A fluffy white interface resulted which was collected and resuspended in the 250 mM sucrose buffer. Protein content was determined by BCA assay (Pierce Chemical Company). The suspension was aliquoted and stored at −70° C.

For the ELISA, the cell membranes were added at a concentration of 400 ng/well to 96 well plates and were dried overnight at 25° C. The plates were washed with 0.5% Triton-X®/phosphate buffered saline (PBS), blocked with 5% fetal bovine serum (FBS)/PBS and washed again. Hybridoma supernatant (40 µl) was diluted in 50 µl PBS and added to the wells overnight at 4° C. After washing, rabbit antimouse IgG (H+L) conjugated to horseradish peroxidase (HRP) (Zymed) was added to the wells for 2 hours at 25° C. The wells were washed with 0.5% Triton-X®/PBS and then incubated in the presence of ABTS (Bio-Rad substrate kit) for 20 minutes before monitoring OD at 405 and 650 nm.

The supernatants of hybridomas generated from the spleen cells of mice immunized with chronically infected cells and acutely infected cells screened positive to both noninfected cell membrane and infected cell membrane in the ELISA, indicating that the antibodies produced by the hybridomas are not HIV-1-specific. Of 1014 hybridomas generated from the spleen cells of mice immunized with infected cell membranes, six of their supernatants reacted strongly with infected cell membrane and reacted very weakly with uninfected cell membrane. Western blots were performed on the supernatants from these hybridoma cell lines and it was determined that three of the six monoclonal antibodies produced by the cell lines bound to HIV-1 p55, one bound to HIV-1 p55 and p24, one to gp120, and the last did not produce a band in the Western blot (data not shown).

One thousand one hundred and eighty-seven hybridomas were generated from the spleen cells of mice immunized with live HIV-1$_{MN}$. Four hybridoma cell lines were selected for further screening based on the results of an ELISA showing that antibodies in the four supernatants reacted strongly with infected cell membrane and very weakly with noninfected cell membrane.

Next, the hybridoma cell lines were screened by immunofluorescence (IFA). Two ml of either uninfected or HIV-1 infected H9 cells (approximately 1×10$^6$ cells/ml) were placed a 10 ml sterile centrifuge tube with 10 ml PBS (without Ca$^{++}$ or Mg$^{++}$). The cells were washed once with 10 ml PBS by filling the tube, vortexing, spinning at 100 rpm for 5 minutes and aspirating all but about 100 µl supernatant leaving a "milky" cell suspension. While working in a laminar flow hood, 51 mm 10-well slides (Cell Line Association) were coated with cell suspension by flooding each well and then drawing the suspension back into the pipet tip. The coated slides were allowed to air dry and were then fixed in methanol at room temperature for 10 minutes. Supernatant from each of the four hybridomas was tested undiluted and at a 1:50 titer (supernatant diluted in 0.02% skim milk) for reactivity with slide preparations of uninfected and infected cells. Fifteen µl of undiluted or diluted supernatant was added to each slide well. The slides were incubated at 37° C. for 30 minutes and submersed in PBS with stirring for 5 minutes. The slides were then quickly rinsed in distilled water and air dried in a laminar flow hood. Sixteen µl goat-anti-mouse IgG (H+L) F(ab)$_2$ fragment (Cappel Biomedical) diluted 1:80 in 0.02% skim milk was added to each well. The slides were again incubated at 37° C. for 30 minutes and then submersed in PBS. The slides were rinsed in 0.01% Evans blue solution in PBS for 5 seconds and rinsed 2 times in distilled water. The slides were examined visually for immunofluorescence. The supernatant from one hybridoma cell line, HB 11614, exhibited greater fluorescence on MN-infected cell lines and lesser fluorescence on uninfected and III$_B$-infected H9 cells.

The hybridoma cell line HB 11614 was subcloned twice and the monoclonal antibody it produced was designated NM03. Mice were intraperitoneally injected with the cell line by standard procedures and monoclonal antibody NM03 was concentrated from the ascites fluid by protein A affinity column purification (Pierce). The isotype of antibody NM03 was determined to be IgM by type specific antisera (Bio-Rad). The antibody (3 mg/ml) was diluted in RPMI 1640 medium with 15% FBS and utilized in the following examples.

EXAMPLE 2

In order to characterize the viral epitope recognized by monoclonal antibody NM03, the antibody was first screened by Western blot analysis for reactivity with purified MN and III$_B$ virion proteins and then by ELISA for reactivity with overlapping peptides corresponding to the amino acid sequence of the V3 loop region of HIV-1$_{MN}$ gp120.

A. Western Blot Analysis

MN and III$_B$ virions purified from culture supernatants of infected H9 cells were disrupted in 1.3% SDS/3% β-mercaptoethanol and then subjected to electrophoresis in a 0.1% SDS/10% polyacrylamide gel. After transfer of the proteins to nitrocellulose paper, strips were incubated overnight with monoclonal antibody NM03 in blocking buffer (0.02M Tris-HCl, pH 7.4, 0.1M NaCl, 5% normal goat serum and 5% nonfat dry milk) at 4° C. and then washed in 0.02M Tris-HCl, pH 7.4, 0.1M NaCl and 0.3% Tween®. The strips were then incubated with biotinylated goat anti-mouse IgG (Zymed) for 1 hour, washed and reacted with $^{125}$I-Streptavidin (Amersham, Arlington Heights, Ill.) for an additional hour at 4° C. Reactivity was monitored by autoradiography.

Monoclonal antibody NM03 exhibited reactivity with MN and III$_B$ viral proteins having an apparent molecular weight of 120 kD, but did not react with any other viral antigens, indicating that the antibody recognizes an epitope of gp120.

B. Epitope Mapping by ELISA

To identify the specific epitope of gp120 recognized by antibody NM03, the antibody was screened by ELISA for reactivity with overlapping peptides corresponding to the V$_3$ loop region of gp120. The peptides, synthesized by Multiple Peptide Systems, San Diego, Calif., corresponded to amino acids 302–316 (V$_3$ loop peptide 1), 312–326 (V$_3$ loop peptide 2) and 322–336 (V$_3$ loop peptide 3) of HIV-1$_{MN}$ gp120. SEQ ID NOs: 2–4 set out the amino acid sequences of the peptides.

The three peptides (250 ng/50 µl 0.1M borate buffer, pH 8.0, per well) were incubated overnight at 37° C. in Immulon 2 plates (Dynatech). The plates were washed with PBS and blocked with PBS/0.1% Tween®/0.1% Bovine Serum Albumin (BSA) for 1 hour at room temperature. The blocking agent was removed and differing amounts of antibody NM03 or mouse IgM (MIgM), diluted in 100 µl HAT media, were added to the plates. The antibody was allowed to react for 2 hours at room temperature. The plates were then washed 10 times with tap water. An HRP-conjugated rabbit anti-mouse second antibody, diluted 1:1000, was brought up in PBS/0.05% Tween®/0.5% BSA, and 100 µl were added per well. The plates were incubated 1 hour at room temperature and then washed 10 times with tap water. ABTS substrate (Bio-Rad) was added for 20 minutes, and the plates were counted at 650 nm. Table 1 sets out the results of the assay utilizing the overlapping peptides wherein the antibody MIgG and HAT medium were negative controls.

TABLE 1

| | Optical density at 650 nm | | | | |
|---|---|---|---|---|---|
| | MIgM HAT | | Antibody NM03 | | |
| Peptide | 500 ng | medium | 4.75 ng | 9.50 ng | 190 ng |
| SEQ ID NO: 2 V$_3$ loop peptide 1 (aa 302–316) CTRPNYNKRKRIHIG | 0.015 | 0.009 | 0.009 | 0.010 | 0.009 |
| SEQ ID NO: 3 V$_3$ loop peptide 2 (aa 312–326) RIHIGPGRAFYTTKN | 0.016 | 0.010 | 0.593 | 1.452 | 2.646 |
| SEQ ID NO: 4 V$_3$ loop peptide 3 (aa 322–336) YTTKNIIGTIRQAHC | 0.021 | 0.011 | 0.009 | 0.011 | 0.014 |

While there was no detectable reactivity over background of monoclonal antibody NM03 with the peptides corresponding to amino acids 302–316 and 322–336 of the V$_3$ loop, binding of the antibody to the peptide representing amino acids 312–326 was apparent. A control antibody, mouse IgM, did not bind to the peptides.

C. Epitope Mapping by Competative Inhibition Assay

To more specfically identify the epitope of the $V_3$ region recognized by antibody NM03, competative inhibition assays were performed to determine binding of the antibody to the MN $V_3$ loop 2 peptide (SEQ ID NO: 3) in the presence of eleven overlapping peptides (SEQ ID NOs: 5 through 15) comprising portions of that amino acid sequence.

One hundred µl of the MN loop 2 peptide (0.5 µg/ml in PBS) was coated on wells of an Immuno 4 plate (Dynatech, Chantilly, Va.) and incubated at room temperature overnight. Wells were then blocked with 250 µl blocking buffer (5% normal rabbit serum in PBS) for 1 hour at 37° C. NM03 antibody and the overlapping peptides were each diluted to 100 µg/ml with blocking buffer. NM03 antibody was then mixed with a peptide solution at 1:1 volume ratio to give an antibody concentration of 5 µg/ml and a peptide concentration of 50 µg/ml. The individual mixtures of NM03 antibody and peptides were allowed to incubate at room temperature for 40 minutes and were then added to different wells (100 µl/well, four duplicates of each peptide) of the Immuno 4 plate for assay. The plate was incubated for 40 minutes at 37° C. Control wells contained 5 µg/ml NM03 antibody and no competing peptide.

The wells were washed four times with washing buffer (0.005% tween-20 in PBS). Secondary antibody, rabbit anti-mouse/horse radish peroxidase-linked antibody, was used at a 1:1000 dilution in blocking buffer. One hundred µl secondary antibody was added per well and the plate was incubated for 1 hour at 37° C. The plate was then washed with washing buffer. The plate was devleoped with 10 µl/well TMB (3, 3', 5, 5'-methyltetrabenzidine) and incubated at room temperature for 7 minutes. The reaction was stopped with 100 µl/well $H_2SO_4$ (0.36N) and the plate was read at 450 nm–650 nm.

The results of the assay are set out below in Table 2.

TABLE 2

|  |  | Percent Inhibition |
|---|---|---|
| SEQ ID NO: 3 | RIHIGPGRAFYTTKN | 99% |
| SEQ ID NO: 5 | HIGPGRAF | 0% |
| SEQ ID NO: 6 | IGPGRAFY | 0% |
| SEQ ID NO: 7 | GPGRAFYT | 0% |
| SEQ ID NO: 8 | PGRAFYTT | 0% |
| SEQ ID NO: 9 | GRAFYTTK | 12% |
| SEQ ID NO: 10 | RAFYTTKN | 92% |
| SEQ ID NO: 11 | AFYTTKNI | 94% |
| SEQ ID NO: 12 | YTTKNIIG | 4% |
| SEQ ID NO: 13 | TKNIIGTI | 0% |
| SEQ ID NO: 14 | NIIGTIRQ | 0% |
| SEQ ID NO: 15 | IGTIRQAH | 0% |

The assay identified the three-dimensional epitope recognized by antibody NM03 as included within the amino acid sequence A-F-Y-T-T-K-N (SEQ ID NO: 1).

EXAMPLE 3

Monoclonal antibody NM03 was tested for the ability to neutralize infection of H9 cells by live HIV-1 laboratory strains MN, MN mutant, III$_B$, 4029, AL and 906 and by live clinical isolates 9435, 9622, 9874, 9938, 9434, 9487, 9489, 9532, 10001, JR/CSF and JR/FL as measured by p24 assay. The amino acid sequences of a portion of the $V_3$ loop region of the III$_B$ and MN mutant laboratory strains and the clinical isolates are set out below in Table 3. The sequences of the $V_3$ loop regions of laboratory strains 4029, AL and 906 have not been determined.

TABLE 3

| Strain or Isolate | $V_3$ Loop Sequence |  |
|---|---|---|
| MN | HIGPGRAFYTTKN | (SEQ ID NO: 3) |
| MN mutant | HIGPGKAFYTTKNIIGTIRQ | (SEQ ID NO: 16) |
| III$_B$ | QRGPGRAFVTIGK | (SEQ ID NO: 17) |
| 9435 | HIGPGRAFVTTRQTIGDIRQ | (SEQ ID NO: 18) |
| 9622 | QRGPGRTFVTIGKIGNMRQ | (SEQ ID NO: 19) |
| 9874 | GIGPGRTVYATDRIIGDIRQ | (SEQ ID NO: 20) |
| 9938 | RVGPGRTLYATRRIIGDIRQ | (SEQ ID NO: 21) |
| 9434 | HIIPGRALYATGKIIGDIRQ | (SEQ ID NO: 22) |
| 9487 | SIGPGRSFYATRQIIGDIRQ | (SEQ ID NO: 23) |
| 9489 | HIGPGRAL(S/A)TGKIIGDIRQ | (SEQ ID NO: 24) |
| 9532 | YIGPGRAFYATDRITGDIRR | (SEQ ID NO: 25) |
| 10001 | SIGPGRAFYTTGRIIGDIRQ | (SEQ ID NO: 26) |
| JR/CSF | HIGPGRAFYTTGEIIGDIRQ | (SEQ ID NO: 27) |
| JR/FL | HIGPGRAFYTTGEIIGDIRQ | (SEQ ID NO: 27) |

For laboratory strains noted above, dilutions of monoclonal antibody NM03 were incubated with 40–100 TCID$_{50}$ of live virus in 96 well plates for 2 hours at 25° C. in RPMI 1640/15% FCS. Purified mouse IgG (Organon Teknika Corp. West Chester, Pa.) was used as a negative control in all p24 assays. H9 cells (2.5×10$^4$ cells) were then added to each well and plates were incubated at 37° C. The H9 cell suspension of each well was diluted in RPMI 1640/15% FCS at 1:4 into another 96 well plate on day 4 and incubated at 37° C. Virus production was determined by p24 assay [Albovini et al., Eds., pp. 15–29 in *Techniques in HIV Research*, Stockton Press, New York, N.Y. (1990)] performed on day 7.

For clinical isolates noted above, dilutions of monoclonal antibody NM03 were incubated with 3–10 TCID$_{50}$ live virus in 96 well plates for 2 hours at 25° C. in RPMI 1640/20% FCS. Purified mouse IgG (Organon Teknika Corp.) was used as a negative control in p24 assays. Peripheral blood mononuclear cells (1.0×10$^5$ cells) were then added to each well and the plates were incubated at 37° C. in RMPI 1640/20% FCS/5% IL-2 (human Interleukin-2, Schiapparelli Biosystems, Columbia, Md.). RPMI 1640/20% FCS/10% IL-2 was added to each well at 1:1 volume on day 4. Virus production was determined by p24 assay performed on day 7.

Results of the assays are presented below in Table 4 wherein the abbreviation "ND" mean not determined and neutralization activity of NM03 is expressed as the concentration of NM03 causing 50% neutralization (concentration of about 0.5 µg/ml indicated by "+++"; concentration of about 5.0 µg/ml indicated by "++"; concentration of >50 µg/ml indicated by "+"; and no neutralization indicated by "−").

TABLE 4

|  | Assay 1 | Assay 2 |
|---|---|---|
| Laboratory Strains |  |  |
| MN | +++ | ++ |
| MNmutant | +++ | +++ |
| IIIB | – | – |
| 4029 | – | – |
| AL | – | ND |
| 906 | – |  |
| Clinical Isolates |  |  |
| 9435 | ++ | ++ |
| 9622 | ++ | ++ |
| 9874 | ++ | + |
| 9938 | ++ | +++ |
| 9434 | + | + |
| 9487 | ++ | + |
| 9489 | – | + |
| 9532 | + | – |
| 10001 | +++ | + |
| JR/CSF | +++ | ++ |
| JR/FL | + | + |

The foregoing results show that monoclonal antibody NM03 neutralizes multiple strains of HIV-1. Variation in results between assays on clinical isolates may be due to differences in preparations of peripheral blood mononuclear cells. While the amino acid sequence of the $V_3$ region of some of the viral isolates varies from A-F-Y-T-T-K-N (SEQ ID NO: 1), the three dimensional structure of the gp120 protein in that region is likely to be similar in the various strains that monoclonal antibody NM-3 neutralizes.

While the present invention has been described in terms of preferred embodiments, it is understood that variations and improvements will occur to those skilled in the art. Therefore, it is intended that the appended claims cover all such equivalent variations which come within the scope of the invention as claimed.

We claim:

1. A monoclonal antibody characterized by the ability to specifically bind to a sequence of amino acids of HIV-1 gp120 or gp160 protein consisting of the sequence set out in SEQ ID NO:1 and the ability to neutralize, in vitro, the infection of H9 cells by live HIV-1 strain MN in p24 assays.

2. The monoclonal antibody according to claim 1 further characterized by being an IgM antibody.

3. A hybridoma cell line which secretes a monoclonal antibody according to claim 1 or 2.

4. The hybridoma cell line having ATCC Accession No. HB 11614.

5. The monoclonal antibody, NM03, produced by the hybridoma cell line of claim 4.

* * * * *

UNITED STATES PATENT AND TRADEMARK OFFICE
CERTIFICATE OF CORRECTION

PATENT NO.   :  5,618,922

DATED        :  April 8, 1997

INVENTOR(S)  :  Ohno et al.

It is certified that error appears in the above-identified patent and that said Letters Patent is hereby corrected as shown below:

At column 2, line 14, replace "supra" with --*supra*--.

At column 3, line 57, replace "in vitro" with --*in vitro*--.

At column 22, line 66, replace "in vitro" with --*in vitro*--.

Signed and Sealed this

Second Day of September, 1997

BRUCE LEHMAN

Attest:

Attesting Officer

*Commissioner of Patents and Trademarks*

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
Ala Phe Tyr Thr Thr Lys Asn
1               5
```

( 2 ) INFORMATION FOR SEQ ID NO:2:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( x i ) SEQUENCE DESCRIPTION: SEQ ID NO:2:

```
Cys Thr Arg Pro Asn Tyr Asn Lys Arg Lys Arg Ile His Ile Gly
1               5                   10                  15
```

( 2 ) INFORMATION FOR SEQ ID NO:3:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( x i ) SEQUENCE DESCRIPTION: SEQ ID NO:3:

```
Arg Ile His Ile Gly Pro Gly Arg Ala Phe Tyr Thr Thr Lys Asn
1               5                   10                  15
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Tyr Thr Thr Lys Asn Ile Ile Gly Thr Ile Arg Gln Ala His Cys
 1               5                  10                  15
```

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
His Ile Gly Pro Gly Arg Ala Phe
 1               5
```

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Ile Gly Pro Gly Arg Ala Phe Tyr
 1               5
```

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Gly Pro Gly Arg Ala Phe Tyr Thr
 1               5
```

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Pro Gly Arg Ala Phe Tyr Thr Thr
 1               5
```

( 2 ) INFORMATION FOR SEQ ID NO:9:

( i ) SEQUENCE CHARACTERISTICS:

(A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:9:

Gly Arg Ala Phe Tyr Thr Thr Lys
    1               5

(2) INFORMATION FOR SEQ ID NO:10:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:10:

Arg Ala Phe Tyr Thr Thr Lys Asn
    1               5

(2) INFORMATION FOR SEQ ID NO:11:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:11:

Ala Phe Tyr Thr Thr Lys Asn Ile
    1               5

(2) INFORMATION FOR SEQ ID NO:12:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:12:

Tyr Thr Thr Lys Asn Ile Ile Gly
    1               5

(2) INFORMATION FOR SEQ ID NO:13:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:13:

Thr Lys Asn Ile Ile Gly Thr Ile
    1               5

(2) INFORMATION FOR SEQ ID NO:14:

(i) SEQUENCE CHARACTERISTICS:
            (A) LENGTH: 8 amino acids
            (B) TYPE: amino acid
            (D) TOPOLOGY: linear (ii) MOLECULE TYPE: peptide ( x i ) SEQUENCE DESCRIPTION: SEQ ID NO:14:

Asn Ile Ile Gly Thr Ile Arg Gln
1               5

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

Ile Gly Thr Ile Arg Gln Ala His
1               5

( 2 ) INFORMATION FOR SEQ ID NO:16:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

His Ile Gly Pro Gly Lys Ala Phe Tyr Thr Thr Lys Asn Ile Ile Gly
1               5                   1 0                 1 5

Thr Ile Arg Gln
        2 0

( 2 ) INFORMATION FOR SEQ ID NO:17:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

Gln Arg Gly Pro Gly Arg Ala Phe Val Thr Ile Gly Lys
1               5                   1 0

( 2 ) INFORMATION FOR SEQ ID NO:18:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

His Ile Gly Pro Gly Arg Ala Phe Val Thr Thr Arg Gln Ile Gly Asp
1               5                   1 0                 1 5

Ile Arg Gln ( 2 ) INFORMATION FOR SEQ ID NO:19:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

Gln Arg Gly Pro Gly Arg Thr Phe Val Thr Ile Gly Lys Ile Gly Asn
1               5                   10                  15

Met Arg Gln ( 2 ) INFORMATION FOR SEQ ID NO:20:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:20:

Gly Ile Gly Pro Gly Arg Thr Val Tyr Ala Thr Asp Lys Arg Ile Ile
1               5                   10                  15

Gly Asp Ile Arg Gln
                20

( 2 ) INFORMATION FOR SEQ ID NO:21:

( i ) SEQUENCE CHARACTERISTICS:
      ( A ) LENGTH: 20 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:21:

Arg Val Gly Pro Gly Arg Thr Leu Tyr Ala Thr Arg Arg Ile Ile Gly
1               5                   10                  15

Asp Ile Arg Gln
            20

( 2 ) INFORMATION FOR SEQ ID NO:22:

( i ) SEQUENCE CHARACTERISTICS:
      ( A ) LENGTH: 20 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:22:

His Ile Glu Pro Gly Arg Ala Leu Tyr Ala Thr Gly Lys Ile Ile Gly
1               5                   10                  15

Asp Ile Arg Gln
            20

( 2 ) INFORMATION FOR SEQ ID NO:23:

( i ) SEQUENCE CHARACTERISTICS:
      ( A ) LENGTH: 20 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:23:

Ser Ile Gly Pro Gly Arg Ser Phe Tyr Ala Thr Arg Gln Ile Ile Gly
1               5                   10                  15

Asp Ile Arg Gln
            20

( 2 ) INFORMATION FOR SEQ ID NO:24:

( i ) SEQUENCE CHARACTERISTICS:
      ( A ) LENGTH: 19 amino acids
      ( B ) TYPE: amino acid
      ( D ) TOPOLOGY: linear ( i i ) MOLECULE TYPE: peptide ( i x ) FEATURE:
      ( B ) LOCATION: 9
      ( D ) OTHER INFORMATION: /note= "The amino acid at position 9
            sometimes is an alanine."

( x i ) SEQUENCE DESCRIPTION: SEQ ID NO:24:

His Ile Gly Pro Gly Arg Ala Leu Ser Thr Gly Lys Ile Ile Gly
   1               5                   10                  15

Asp Ile Arg Gln ( 2 ) INFORMATION FOR SEQ ID NO:25:

( i ) SEQUENCE CHARACTERISTICS:
      ( A ) LENGTH: 20 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:25:

Tyr Ile Gly Pro Gly Arg Ala Phe Tyr Ala Thr Asp Arg Ile Thr Gly
   1               5                   10                  15

Asp Ile Arg Arg
                 20

( 2 ) INFORMATION FOR SEQ ID NO:26:

( i ) SEQUENCE CHARACTERISTICS:
      ( A ) LENGTH: 20 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:26:

Ser Ile Gly Pro Gly Arg Ala Phe Tyr Thr Thr Gly Arg Ile Ile Gly
   1               5                   10                  15

Asp Ile Arg Gln
                 20

( 2 ) INFORMATION FOR SEQ ID NO:27:

( i ) SEQUENCE CHARACTERISTICS:
      ( A ) LENGTH: 20 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:27:

His Ile Gly Pro Gly Arg Ala Phe Tyr Thr Thr Gly Glu Ile Ile Gly
   1               5                   10                  15

Asp Ile Arg Gln
                 20